United States Patent
Loescher

(10) Patent No.: US 8,124,819 B2
(45) Date of Patent: Feb. 28, 2012

(54) OLIGOMERIZATION PROCESS

(75) Inventor: Mitchell E. Loescher, Houston, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 521 days.

(21) Appl. No.: 12/350,539

(22) Filed: Jan. 8, 2009

(65) Prior Publication Data

US 2010/0174126 A1    Jul. 8, 2010

(51) Int. Cl.
   *C07C 2/06*  (2006.01)
   *C07C 5/25*  (2006.01)

(52) U.S. Cl. ......... 585/329; 585/330; 585/331; 585/332

(58) Field of Classification Search ............ 585/329, 585/330, 331, 332
See application file for complete search history.

(56) References Cited

U.S. PATENT DOCUMENTS

| | | | |
|---|---|---|---|
| 3,686,354 A * | 8/1972 | Hervert ........................ | 585/331 |
| 3,960,978 A | 6/1976 | Givens et al. | |
| 4,021,502 A | 5/1977 | Plank et al. | |
| 4,215,011 A * | 7/1980 | Smith, Jr. ...................... | 422/211 |
| 4,242,530 A | 12/1980 | Smith, Jr. | |
| 4,313,016 A | 1/1982 | Manning | |
| 4,375,576 A | 3/1983 | Smith, Jr. | |
| 4,540,839 A | 9/1985 | Keyworth et al. | |
| 4,695,664 A | 9/1987 | Whittle | |
| 4,956,514 A | 9/1990 | Chu | |
| 5,003,124 A | 3/1991 | Smith, Jr. et al. | |
| 5,087,780 A | 2/1992 | Arganbright | |
| 5,510,555 A | 4/1996 | Brunelli et al. | |
| 5,789,643 A | 8/1998 | Herwig et al. | |
| 6,143,942 A | 11/2000 | Verrelst et al. | |
| 6,242,661 B1 * | 6/2001 | Podrebarac et al. .......... | 585/664 |
| 6,335,473 B1 | 1/2002 | Bakshi et al. | |
| 6,501,001 B2 | 12/2002 | Commereuc et al. | |
| 6,613,108 B1 | 9/2003 | Aittamaa et al. | |
| 7,145,049 B2 | 12/2006 | Loescher et al. | |
| 7,161,053 B2 * | 1/2007 | Beckmann et al. .......... | 585/530 |
| 2006/0235252 A1 | 10/2006 | Gartside et al. | |
| 2006/0235255 A1 | 10/2006 | Gartside et al. | |

FOREIGN PATENT DOCUMENTS

GB    2325237 A  * 11/1998

OTHER PUBLICATIONS

International Search Report and Written Opinion issued May 26, 2010 in corresponding International Application PCT/US2009/064181 (7 pages).

* cited by examiner

*Primary Examiner* — Thuan Dinh Dang
(74) *Attorney, Agent, or Firm* — Osha • Liang LLP

(57) ABSTRACT

A process for oligomerization of isobutene, the process including: feeding a hydrocarbon stream comprising n-butane, 1-butene, 2-butene, isobutane, and isobutene to a catalytic distillation reactor system comprising a hydroisomerization catalyst; feeding hydrogen to the catalytic distillation reactor system; concurrently in the catalytic distillation reactor system: contacting the 1-butene with the hydrogen in the presence of the hydroisomerization catalyst to convert at least a portion of the 1-butene to 2-butene; separating the isobutane and the isobutene from the n-butane and the 2-butene; recovering the isobutane and the isobutene from the catalytic distillation reactor system as an overheads fraction; recovering the n-butane and the 2-butene from the catalytic distillation reactor system as a bottoms fraction; contacting the overheads fraction in an oligomerization reaction system with an oligomerization catalyst to convert a portion of the isobutene to oligomers.

13 Claims, 2 Drawing Sheets

OLIGOMERIZATION PROCESS

BACKGROUND OF DISCLOSURE

1. Field of the Disclosure

Embodiments herein relate generally to oligomerization of isoolefins. More specifically, embodiments disclosed herein relate to processing of mixed $C_4$ hydrocarbon streams to produce oligomers of isoolefins and linear butene recovery.

2. Background

Olefins produced in various refining operations, such as a steam cracker or an FCC, can be used as a valuable feedstock for gasoline blending. Depending on the source, olefins can vary in size, degree of branching, and position of the double bond. In some processes, olefins may be available as a mixed stream containing straight and branched olefins of various length and double bond position together with paraffins, dienes and acetylenes.

In order to meet the fuel blending requirements, such as octane rating or vapor pressure requirements, smaller olefin molecules must be upgraded to produce longer chain molecules. One commonly used method of upgrading smaller olefin molecules, such as $C_2$ to $C_5$ olefins, is an oligomerization reaction.

Oligomerization reactions involve contacting an olefin with a catalyst in order to produce a longer chain molecule. An oligomer can consist of two or more constituent olefin molecules. For example, dimerization is a type of oligomerization reaction that is limited to a combination of only two olefin molecules. If the olefin feed contains only one type of olefin, a dimer product is formed. If the olefin feed contains two or more different olefins or olefin isomers, a codimer product may also be formed.

Specifically, $C_4$ olefin dimerization is widely used for producing isooctene, an intermediate that can be hydrogenated to produce isooctane, a high-value gasoline blending additive. Several representative olefin dimerization reactions are shown below:

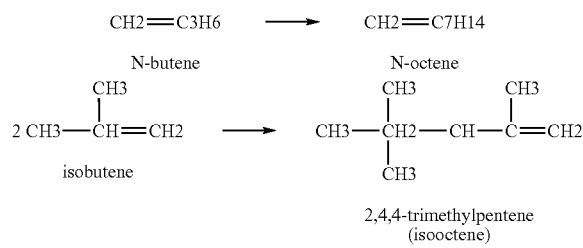

A gas phase olefin oligomerization process is disclosed in U.S. Pat. Nos. 3,960,978 and 4,021,502, where $C_2$ to $C_5$ olefins, fed as either pure olefins or in admixture with paraffins, are oligomerized via contacted with a zeolite fixed catalyst bed. Other oligomerization processes are disclosed in, for example, U.S. Pat. Nos. 4,242,530, 4,375,576, 5,003,124, and 7,145,049, among others In any type of oligomerization reaction, the oligomerization catalyst activity can be drastically reduced due to poisoning, fouling, and coking frequently caused by impurities present in the olefin feed stream. Furthermore, various additives and impurities that may be present in the olefin feed can participate in side reactions leading to formation of undesirable byproducts. For example, the presence of normal butene in the isobutene oligomerization process to produce isooctene dimer can lead to formation of undesirable $C_8$ codimers.

Formation of $C_8$ codimers can adversely affect an operator in two major ways. First, it reduces the effective yield of the $C_8$ dimer target product, thus increasing the dimerization reactor feedstock and operating costs. Second, it may require additional costs associated with separation and removal of $C_8$ codimers from the $C_8$ dimer product.

Oligomerization reaction additives, such as a reaction moderator, can also participate in undesirable side reactions with the olefin or with the dimerization product. Moderator is frequently added to the oligomerization reaction in order to increase the dimer selectivity by limiting the extent of oligomerization reaction to the dimer stage. Suitable moderators include oxygenates, such as water, primary, secondary and tertiary alcohols and ethers. However, as a trade-off to achieving high dimer selectivity, a portion of the moderator can react with an olefin or a dimerization product to form heavy oxygenates, for example, MSBE. A representative reaction of an olefin with a moderator to form a heavy oxygenate is shown below:

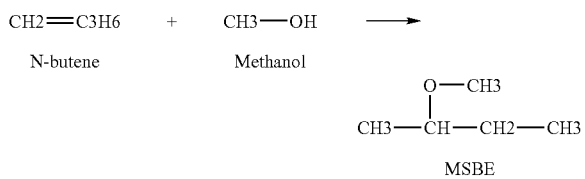

Similar to other types of side reactions, the reaction of moderator to produce heavy oxygenates, such as MSBE, can also reduce the $C_8$ dimer product yield and require additional separation costs in order to maintain the desired product purity.

Accordingly, there still exists a need for an improved methods for producing oligomers of isoolefins.

SUMMARY OF THE DISCLOSURE

In one aspect, embodiments disclosed herein relate to a process for oligomerization of isobutene, the process including: feeding a hydrocarbon stream comprising n-butane, 1-butene, 2-butene, isobutane, and isobutene to a catalytic distillation reactor system comprising a hydroisomerization catalyst; feeding hydrogen to the catalytic distillation reactor system; concurrently in the catalytic distillation reactor system: contacting the 1-butene with the hydrogen in the presence of the hydroisomerization catalyst to convert at least a portion of the 1-butene to 2-butene; separating the isobutane and the isobutene from the n-butane and the 2-butene; recovering the isobutane and the isobutene from the catalytic distillation reactor system as an overheads fraction; recovering the n-butane and the 2-butene from the catalytic distillation reactor system as a bottoms fraction; contacting the overheads fraction in an oligomerization reaction system with an oligomerization catalyst to convert a portion of the isobutene to oligomers.

Other aspects and advantages will be apparent from the following description and the appended claims.

DETAILED DESCRIPTION

Figure 1:
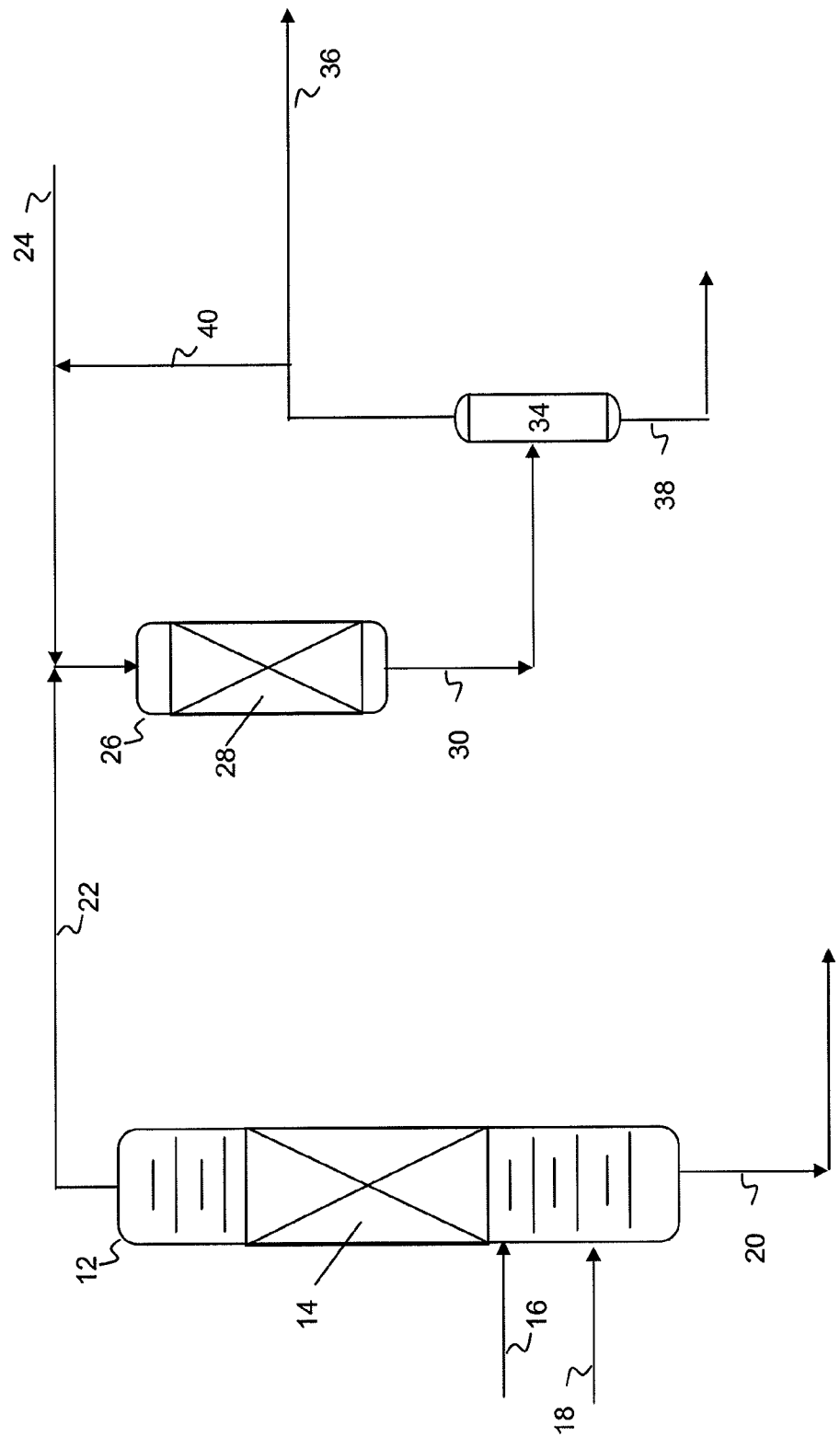
FIG. 1 is a simplified flow diagram of an oligomerization process according to embodiments disclosed herein.

In one aspect, embodiments herein relate generally to oligomerization of isoolefins. More specifically, embodiments disclosed herein relate to processing of mixed $C_4$ hydrocarbon streams to produce oligomers of isoolefins and linear butene recovery generally to selective dimerization of $C_4$ olefins. For example, a hydrocarbon stream containing 1-butene, 2-butene, isobutane, and isobutene may be processed according to embodiments disclosed herein to advantageously recover one or more of isobutene oligomers, isobutane, and 2-butene.

As used in embodiments disclosed herein, "catalytic distillation reactor system" refers to a system for concurrently reacting compounds and separating the reactants and the products using fractional distillation. In some embodiments, the catalytic distillation reactor system may comprise a conventional catalytic distillation column reactor, where the reaction and distillation are concurrently taking place at boiling point conditions. In other embodiments, the catalytic distillation reactor system may comprise a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

A C4-containing hydrocarbon stream, such as a C4 naphtha cut, a C4-C5 naphtha cut, or a C4-C6 naphtha cut may be fed to a reactor for the hydroisomerization of 1-butene to 2-butene, thus allowing for the separation of isobutene from the linear olefin 2-butene. The hydroisomerization may be carried out in a fixed bed reactor as well as in a catalytic distillation reaction system. For example, in some embodiments, a feed containing 1-butene, 2-butene, isobutene, n-butane, and isobutane may be fed to a catalytic distillation reaction system containing at least one bed of hydroisomerization catalyst for the concurrent hydroisomerization of 1-butene to 2-butene and the fractionation of isobutane and isobutene, recovered as an overheads, from the heavier hydrocarbons in the feed stream, including the n-butane and 2-butene, recovered as a bottoms fraction. Feed and catalyst locations may be positioned so as to preferentially contact the 1-butene with the hydroisomerization catalyst. For example the hydrocarbon may be fed to a location below the hydroisomerization catalyst, allowing the 1-butene to distill up into the catalyst bed while distilling the 2-butene down the column, away from the catalyst bed. In other embodiments, a hydroisomerized effluent from a fixed bed reactor may be fed to a conventional distillation column to result in similar overheads and bottoms fractions.

The resulting bottoms fraction, including the 2-butene and the n-butane, may be lean in 1-butene, isobutane, and isobutene. For example, depending upon the severity of the distillation conditions used, the bottoms fraction may contain less than 1 weight percent total of 1-butene, isobutane, and isobutene; less than 0.5 weight percent total in other embodiments; less than 0.1 weight percent total in other embodiments; and less than 500 ppm total in yet other embodiments.

The overheads fraction, including the isobutene and isobutane may also contain some unreacted 1-butene. In some embodiments, the overheads fraction may contain less than 1000 ppm 1-butene; less than 500 ppm in other embodiments; less than 250 ppm in other embodiments; less than 100 ppm in other embodiments; and less than 50 ppm in yet other embodiments.

The overhead fraction may then be oligomerized to form dimers and trimers of isobutene in an oligomerization reaction zone. Oligomerization, for example, may be carried out using a selectivity moderator, such as oxygen-containing reaction moderators including methanol, water, ethanol, and tertiary ethers, among others. Due to the low presence of 1-butene in the overheads fraction, the resulting oligomer stream may include a low amount of oligomerization reaction byproducts, such as methyl sec-butyl ether, which may be formed by the reaction of linear butenes in the oligomerization feed with methanol, for example. The low concentration of linear butenes in the oligomerization feed may result in an oligomerization effluent containing less than 1000 ppm methyl sec-butyl ether in some embodiments; less than 500 ppm methyl sec-butyl ether in other embodiments; less than 250 ppm methyl sec-butyl ether in other embodiments; less than 100 ppm methyl sec-butyl ether in other embodiments; and less than 50 ppm methyl sec-butyl ether in yet other embodiments.

As described above, processes disclosed herein may provide for the isomerization of 1-butene to 2-butene, producing additional quantities of 2-butene which may be used in various downstream processes. Additionally, due to the decreased linear butene content of the oligomerization feed, processes disclosed herein may result in low levels of undesired oligomerization reaction byproducts, such as methyl sec-butyl ether, reducing separation requirements prior to use of the oligomer product in downstream operations.

Hydroisomerization

Hydroisomerization may be carried out, for example, in a catalytic distillation reactor system containing at least one distillation reaction zone of hydroisomerization catalyst, such as that disclosed in U.S. Pat. Nos. 5,087,780 and 6,242,661 and U.S. Patent Application Publication Nos. 2006-0235252 and 20060235255.

A C4 feed stream may be fed to a hydroisomerization reactor. A typical C4 feed stream to the hydroisomerization reactor may contain 2-50 weight percent 1-butene, 2-50 weight percent 2-butene, 2-50 weight percent isobutene, 2-50 weight percent isobutane, and 2-50 weight percent n-butane, the total weight percent being 100. If present, butadiene is present at a concentration of less than 1500 ppm by weight. Hydrogen is fed directly to the hydroisomerization reactor or may be combined with the C4 feed stream prior to introduction of the components to the hydroisomerization reactor. Multiple hydrogen injection points may also be used to minimize the hydrogenation of the olefins.

In the hydroisomerization reactor, 1-butene is hydroisomerized into 2-butene using any suitable hydroisomerization catalyst. Examples of such catalysts are noble metals, such as palladium, supported on alumina, as well as sulfided nickel supported on alumina. Additives to the metals including Ag, Au, etc can be used to modify the reaction characteristics.

For fixed bed hydroisomerization reactors pressures may be in the range from 2 to 30 barg in some embodiments, and from 5-18 barg in other embodiments. Typical reactor inlet temperatures are 80-250° F. in some embodiments, and 120-180° F. in other embodiments. The reactor effluent may then be fed to a deisobutenizer tower for the separation of isobutene and isobutane from the 2-butene and heavier hydrocarbons. The reactor effluent optionally may be vented to remove excess hydrogen from the stream before being fed to the deisobutenizer tower.

For catalytic distillation hydroisomerization systems, column temperatures may range from 80-220° F. in some embodiments, and from 100-180° F. in other embodiments. Column operating pressures may range from 2-12 barg in some embodiments, and from 3-8 barg in other embodiments. In other embodiments, combinations of fixed bed reactors and catalytic distillation reaction systems may be used.

For example, to further hydroisomerize the remaining 1-butene to 2-butene in the deisobutenizer tower, a catalyst section may be included at the upper end of the deisobutenizer tower. The single catalyst stage may be located within a section of high driving force for the hydroisomerization reaction. Depending on the tower operation, this may be in the upper end of the deisobutenizer tower. The type of catalyst used in the deisobutenizer can be the same as, or different from, the catalyst used in the hydroisomerization reactor and can be installed in one or more beds. The 2-butene formed in this hydroisomerization reaction moves downwardly through the deisobutenizer tower and out in the bottoms stream.

Steam cracker C4 streams may contain appreciable quantities of butadiene and therefore, in some embodiments, processes disclosed herein may require inclusion of a selective hydrogenation unit to convert a majority of the butadiene to butenes upstream of the hydroisomerization reactor. Refinery C4 streams have a low butadiene content that can be processed within the hydroisomerization unit, and thus inclusion of a selective hydrogenation unit is not required. The inclusion of a fractionator upstream from the deisobutenizer provides for the removal of heavy materials that enter the system along with the C4s. Refinery C4 streams often contain heavier sulfur compounds including dimethyl disulfide (DMDS) and diethyl disulfide (DEDS), both of which can be removed by a first fractionating tower.

Oligomerization

The overheads fraction from the deisobutenizer or the catalytic distillation hydroisomerization system, or a portion thereof, may then be fed to an oligomerization unit to oligomerize the isobutene. Oligomerization may be carried out, for example, in a partial liquid phase in the presence of an acid cation resin catalyst, either in straight pass type reaction, such as that disclosed in U.S. Pat. Nos. 4,313,016, 4,540,839, 5,003,124, and 6,335,473, or in a catalytic distillation reaction where there is both a vapor and a liquid phase and a concurrent reaction/fractionation.

The primary oligomer products are dimers and trimers of isoolefins. For example, isobutene may be oligomerized to form a $C_8$ or $C_{12}$ tertiary olefin. In some embodiments, the oligomers have 8 to 16 carbon atoms and correspond to oligomers prepared from $C_4$ olefins.

The oligomerization of isoolefins may be carried out in a partial liquid phase in the presence of an acid cation resin catalyst either in straight pass type reaction or in a catalytic distillation reaction where there is both a vapor and liquid phase and a concurrent reaction/fractionation. Catalysts used in oligomerization reactors may include acid resins, such as AMBERLYST 15 (available from Rohm and Haas) or related oleum derived resins and may include phosphoric acid derived catalysts, such as those known to the industry as SPA (solid phosphoric acid) catalysts.

Oxygen-containing moderators may be used to influence the selectivity of the oligomerization reaction to the dimer product. Oxygen-containing moderators useful in embodiments disclosed herein may include water as well as tertiary alcohols and ethers. For example, the oxygen-containing moderator may include at least one of: water, tertiary butyl alcohol, methanol, methyl tertiary butyl ether, ethanol, and ethyl tertiary butyl ether.

Oligomerization reactions carried out in the presence of the oxygen-containing moderators may concurrently produce oligomers, such as dimers and trimers of the isoolefins, and various oxygen-containing byproducts due to reaction of a moderator with an isoolefin or an isoolefin oligomer, such as a dimer or trimer. For example, the oxygenated oligomerization byproducts may include $C_5$-$C_{16}$ ethers and $C_5$-$C_{12}$ alcohols. In some embodiments, isobutene may react with a moderator to form secondary ethers, such as methyl sec-butyl ether, which may be undesireable.

The oligomerization reactors used in embodiments disclosed herein may include any physical devices or a combination of two or more devices. The reactors may have various internal devices for vapor-liquid separation and vapor/liquid traffic. Any type of reactor may be used to carry out the reactions described herein. The examples of reactors suitable for carrying out the reactions involving isoolefin dimerization or oligomerization reactions may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors. Multiple reactor systems useful in embodiments disclosed herein may include a series of multiple reactors or multiple reactors in parallel for the first reaction zone. A person of ordinary skill in the art would recognize that other types of reactors may also be used.

For example, straight pass oligomerization reactors may be used, such as disclosed in U.S. Pat. Nos. 4,313,016; 4,540, 839; 5,003,124; and 6,335,473. The oligomerization of propylene may be carried out, for example, in tubular reactors at 330-482° F. and 1000 to 1215 psig using supported phosphoric acid (sPa), metal complexes (U.S. Pat. Nos. 5,510,555; 4,695,664 and 6,501,001) and various zeolites, especially ZSM-22, ZSM-57 (U.S. Pat. No. 6,143,942) and MCM-22 (U.S. Pat. No. 4,956,514) which has been shown to have favorable characteristics for the oligomerization of propylene at lower pressures and temperatures than the other catalysts. In such straight pass reactors, the effluent from the oligomerization reaction zone may include the oligomers and one or more of unreacted isobutene, unreacted 1-butene, isobutane, oxygen-containing reaction moderators, and oxygenated oligomerization byproducts.

As another example, the oligomerization may be carried out in a catalytic distillation type reaction, such as that disclosed in U.S. Pat. Nos. 4,242,530 or 4,375,576. During catalytic distillation, the oligomers and the oxygenated oligomerization byproducts may be fractionated from unreacted isoolefins and other light hydrocarbons. The unreacted isobutene, 1-butene, if present, and isobutane may be recovered as an overheads fraction, a fraction of which may also be used as column reflux. The oligomers and oxygenated oligomerization byproducts may be recovered as a bottoms fraction, where the bottoms is herein defined as the oligomerization reactor effluent from the catalytic distillation column. Depending upon the type of reaction moderator used and the conditions in the distillation column reactor, the oxygen-containing reaction moderator may be recovered with either or both the overheads fraction and the bottoms fraction.

In some embodiments, the reaction effluent, including the oligomers and the oxygenated oligomerization byproduct, or a portion thereof, may then be fractionated to recover a fraction including the oxygenated oligomerization byproduct and the trimers and a fraction including the dimers.

When the reactor effluent further includes unreacted isoolefin and/or oxygen-containing moderator, such as from a straight-pass reactor, the reactor effluent may be fractionated to additionally recover a fraction containing the oxygen-containing moderator and/or the unreacted isoolefin, which may be recycled to the oligomerization reaction zone in some embodiments. Any separation scheme to produce three separate fractions, including a light fraction (moderator and/or unreacted isoolefin), a medium fraction (dimers), and a heavy fraction (trimers and oxygenated oligomerization byproducts), may be used.

For example, in some embodiments, the desired fractions may be obtained using a first distillation column to separate the lights fraction from the medium and heavy fractions followed by separation of the medium and heavy fractions. In other embodiments, the desired fractions may be obtained using a first distillation column to separate the heavy fraction from the light and medium fraction followed by separation of the light and medium fractions. In yet other embodiments, a single distillation column or a divided wall distillation column including a side draw may be used to provide the desired separations. One skilled in the art would recognize that other means to obtain the desired fractions can be used.

Referring now to FIG. 1, a process for oligomerizing isobutene according to embodiments disclosed herein is illustrated. Mixed $C_4$s, including isobutene, isobutane, 1-butene, and 2-butene, and hydrogen may be fed to a first catalytic distillation reactor system 12, containing a bed of hydroisomerization catalyst 14, via flow lines 16 and 18, respectively. Concurrently in catalytic distillation reactor system 12, (a) a portion of the 1-butene may be contacted in the presence of hydrogen with hydroisomerization catalyst 14 to convert a portion of the 1-butene to 2-butene; and (2) the isobutene and isobutane may be separated from the n-butane and the 2-butene. The n-butane and the 2-butene may be recovered as a bottoms fraction via flow line 20, and the isobutene and the isobutane may be recovered as an overheads fraction via flow line 22.

The overhead fraction may then be fed via flow line 22, along with moderator fed via flow line 24, to a fixed bed oligomerization reaction system 26 containing an oligomerization catalyst 28. The isobutene reacts in the presence of the oligomerization catalyst 28 contained in oligomerization reaction zone 26 to convert a portion of the isobutene to oligomers, including dimers and trimers of isobutene. As a side reaction, the moderator may react with a portion of at least one of the isoolefin and any 1-butene recovered in the overheads fraction from the hydroisomerization reactor 12 in oligomerization reaction zone 26 to form oxygenated oligomerization byproducts, such as methyl sec-butyl ether. Effluent, containing the oligomerization product and the oxygenated oligomerization byproducts, as well as any unreacted moderator and isoolefin, may be recovered from oligomerization reaction zone 26 via flow line 30.

The reaction effluent may then be fed to a separation unit to separate the reaction effluent into desired fractions. For example, the reaction effluent may be fed via flow line 30 to a first distillation column 34 to separate the moderator and unreacted isoolefin from the oligomers and the oxygenated oligomerization byproducts. The unreacted isoolefin and moderator may be recovered as an overheads fraction via flow line 36, and the oligomers and oxygenated oligomerization byproducts may be recovered via flow line 38. If desired, the moderator and unreacted isoolefin may be recycled to the oligomerization reaction zone via flow line 40.

Figure 2:
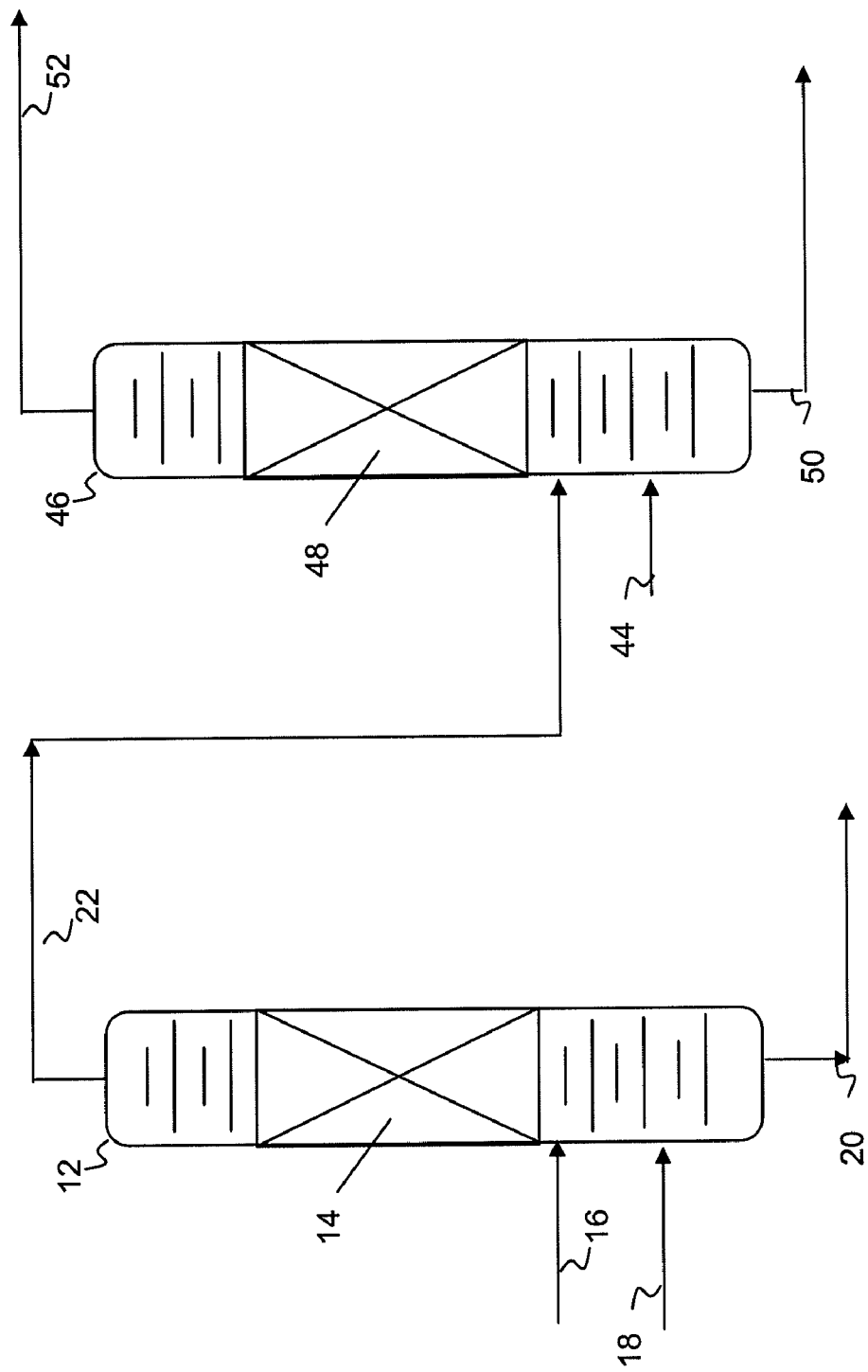
FIG. 2 is a simplified flow diagram of oligomerization process according to embodiments disclosed herein.

Referring now to FIG. 2, where like numerals represent like parts, a process for oligomerizing isoolefins according to embodiments disclosed herein is illustrated. Mixed $C_4$s, including isobutene, isobutane, 1-butene, and 2-butene, and hydrogen may be fed to a first catalytic distillation reactor system 12, containing a bed of hydroisomerization catalyst 14, via flow lines 16 and 18, respectively. Concurrently in catalytic distillation reactor system 12, (a) a portion of the 1-butene may be contacted in the presence of hydrogen with hydroisomerization catalyst 14 to convert a portion of the 1-butene to 2-butene; and (2) the isobutene and isobutane may be separated from the n-butane and the 2-butene. The n-butane and the 2-butene may be recovered as a bottoms fraction via flow line 20, and the isobutene and the isobutane may be recovered as an overheads fraction via flow line 22.

The overhead fraction may then be fed via flow line 22, along with moderator fed via flow line 44, to a catalytic distillation reaction system 46 containing an oligomerization catalyst 48. The isobutene reacts in the presence of the oligomerization catalyst 48 contained in oligomerization reaction zone 46 to convert a portion of the isobutene to oligomers, including dimers and trimers of isobutene. As a side reaction, the moderator may react with a portion of at least one of the isoolefin and any 1-butene recovered in the overheads fraction from the hydroisomerization reactor 12 in oligomerization reaction zone 46 to form oxygenated oligomerization byproducts, such as methyl sec-butyl ether. Concurrent with the oligomerization reaction, the oligomers, including dimers and trimers, as well as heavy reaction byproducts distill downward and may be recovered as a bottoms fraction via flow line 50, and the isobutane and any unreacted isobutene and 1-butene, if present and unreacted, may distill upward and be recovered via flow line 52.

The oligomerization effluent, including dimers and trimers produced via the processes of FIGS. 1 and 2, may be further separated, if desired, and/or used as a raw material for various downstream processes. For example, a resulting dimer fraction may be used as a raw material for the production of various chemicals, such as herbicides and pesticides. In other embodiments, the dimers or oligomers may be fed to an alkylation system, where the oligomers may dissociate into constituent olefins and react with an alkane to produce an alkylate in the gasoline-boiling range. The dimer may also be hydrogenated to form gasoline-range hydrocarbons, such as octane, nonane, and other hydrocarbons. In yet other embodiments, the dimer containing stream may be used as a gasoline-range hydrocarbon blendstock without hydrogenation or alkylation. Due to the low concentration of linear butenes in the feed to the oligomerization unit, it may not be necessary to remove the oxygenated byproducts from the oligomerization effluent prior to these downstream processes.

As described above, embodiments disclosed herein relate to hydroisomerization and separation of a mixed $C_4$ hydrocarbon stream, where the subsequent oligomerization of isobutene may result in a significantly reduced amount of undesired reaction byproducts as a result of low concentrations of linear butenes in the oligomerization feed. For example, when an oligomerization reaction moderator is used, the linear butenes in the feed can react with the moderator via to form a heavy oxygenate, such as methyl sec-butyl ether. Embodiments disclosed herein may avoid or limit the formation of such unwanted byproducts resulting from linear butenes.

One advantage of using oligomerization processes according to embodiments disclosed herein is a reduced cost associated with separation and recovery of the undesired byproducts from the $C_8$ dimer product. The reduction of linear butenes in the oligomerization feed reduces formation of these impurities and thus may reduce or eliminate the need to conduct further separations prior to use of the oligomer product in downstream operations.

Another advantage of using processes according to embodiments disclosed herein is the increased yield of the $C_8$ dimer product. As the undesirable side reaction between the linear butenes and the isobutene is minimized, the amount of isobutene that is converted to the undesirable $C_8$ codimer is reduced and the amount of isobutene that is converted to the target $C_8$ dimer product is increased.

Yet another advantage of using processes according to embodiments disclosed herein is the enhanced recovery of 2-butene as a chemical feedstock for other reactions. For example, 2-butene may be preferred over 1-butene for use in metathesis. As the mixed $C_4$ stream is contacted in the presence of hydrogen and the hydroisomerization catalyst in the catalytic distillation reactor system, the majority of 1-butene in the mixed $C_4$ stream is converted into 2-butene. Thus, processes according to embodiments disclosed herein may provide additional 2-butene as feedstock for other downstream processes.

Yet another advantage of using processes according to embodiments disclosed herein is production of a relatively pure isobutane stream that may be used as an alkylation feedstock. As isobutane and isobutene are separated from the mixed $C_4$ feed in the hydroisomerization reactor system, isobutane is the only impurity fed to the oligomerization reaction system along with the isobutene in a significant amount. Due to proximity of the boiling points of isobutane and isobutene and the low reactivity of isobutane in the oligomerization reaction, the two oligomerization feed components typically do not require pre-separation. As the predominant portion of isobutene is consumed in the oligomerization reaction, a relatively pure isobutane can be easily separated from the $C_8$ dimer product using boiling point separation.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:

1. A process for oligomerization of isobutene, the process comprising:
   feeding a hydrocarbon stream comprising n-butane, 1-butene, 2-butene, isobutane, and isobutene to a catalytic distillation reactor system comprising a hydroisomerization catalyst;
   feeding hydrogen to the catalytic distillation reactor system;
   concurrently in the catalytic distillation reactor system:
      contacting the 1-butene with the hydrogen in the presence of the hydroisomerization catalyst to convert at least a portion of the 1-butene to 2-butene;
      separating the isobutane and the isobutene from the n-butane and the 2-butene;
   recovering the isobutane and the isobutene from the catalytic distillation reactor system as an overheads fraction, wherein the overheads comprises less than 250 ppm 1-butene;
   recovering the n-butane and the 2-butene from the catalytic distillation reactor system as a bottoms fraction;
   contacting the overheads fraction in an oligomerization reaction system with an oligomerization catalyst in the presence of an oxygen-containing moderator to convert a portion of the isobutene to oligomers, and react a portion of the isobutene with the oxygen-containing moderator to form oxygenated byproducts;
   recovering an effluent from the oligomerization reaction system comprising: the oliogomers, isobutane, unreacted isobutene, and the oxygenated byproducts;
   separating a fraction comprising the oligomers and the oxygenated byproducts from the isobutane and the unreacted isobutene;
   hydrogenating or alkylating the fraction comprising the oligomers without further separation of the oxygenated byproducts from the oligomers.

2. The process of claim 1, wherein the hydrocarbon stream comprises at least one of a C4 naphtha cut, a C4-C5 naphtha cut, and a C4-C6 naphtha cut.

3. The process of claim 1, wherein the first overheads comprises less than 5 ppm 1-butene.

4. The process according to claim 3, wherein the moderator comprises methanol, the concurrently further comprising:
   reacting at least a portion of the methanol with at least a portion of the 1-butene to form methyl sec-butyl ether.

5. The process according to claim 1,
   wherein the fraction comprising the oligomers contains less than 250 ppm methyl sec-butyl ether.

6. The process according to claim 1, wherein the bottoms fraction from the catalytic distillation reactor system containing the hydroisomerization catalyst comprises less than 1 wt. % of isobutene, isobutane, and 1-butene.

7. The process according to claim 1, wherein the hydroisomerization catalyst comprises at least one of palladium supported on alumina and sulfided nickel supported on alumina.

8. The process according to claim 1, wherein the catalytic distillation reactor system operates at a temperature in the range from about 80° F. to about 300° F.

9. The process according to claim 1, wherein the catalytic distillation reactor system operates at a pressure in the range from about 30 psig to about 450 psig.

10. The process of claim 1, further comprising blending at least a portion of the effluent, a hydrogenated product, or an alkylate product to form a gasoline-range fuel.

11. The process according to claim 1, wherein the oligomerization reaction system comprises a second catalytic distillation reaction system, the contacting the overheads fraction further comprising:
   separating the oligomers from unreacted isobutene and isobutane by fractionation;
   recovering the unreacted isobutene and isobutane as a second overheads fraction; and
   recovering the oligomers as a second bottoms fraction.

12. The process according to claim 11, wherein the second overheads fraction comprises less than 1000 ppm unreacted isobutene.

13. The process according to claim 11, further comprising feeding at least a portion of the second overheads fraction to an alkylation system.

* * * * *